US011058586B2

(12) United States Patent
Sommers

(10) Patent No.: US 11,058,586 B2
(45) Date of Patent: Jul. 13, 2021

(54) HARD HAT ADAPTER FOR A WELDING FACE MEMBER

(71) Applicant: ILLINOIS TOOL WORKS INC., Glenview, IL (US)

(72) Inventor: Eric T. Sommers, Appleton, WI (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 0 days.

(21) Appl. No.: 15/967,425

(22) Filed: Apr. 30, 2018

(65) Prior Publication Data

US 2018/0242678 A1 Aug. 30, 2018

Related U.S. Application Data

(62) Division of application No. 14/738,339, filed on Jun. 12, 2015, now abandoned.

(51) Int. Cl.
*A61F 9/06* (2006.01)
*A42B 3/22* (2006.01)

(52) U.S. Cl.
CPC ............ *A61F 9/06* (2013.01); *A42B 3/225* (2013.01); *A42B 3/222* (2013.01)

(58) Field of Classification Search
CPC .......... A42B 3/222; A42B 3/225; A42B 3/04; A42B 3/18; A42B 3/185; A42B 3/20; A42B 3/22; A42B 3/221; A42B 3/223; A42B 3/224; A42B 3/228; A61F 9/06; A61F 9/025; A61F 9/061; G02C 3/02
USPC ........ 2/422, 7, 9, 8.1, 424, 10, 6.3, 6.5, 6.7, 2/8.2
See application file for complete search history.

(56) References Cited

U.S. PATENT DOCUMENTS

| | | | |
|---|---|---|---|
| 1,182,367 A * | 5/1916 | Gravell | A61F 9/06 2/8.2 |
| 1,338,022 A | 4/1920 | Lamoreaux | |
| 1,601,830 A | 10/1926 | Huntsman | |
| 1,947,786 A | 2/1934 | Lueck | |
| 1,994,103 A | 3/1935 | Huey | |
| 2,167,969 A * | 8/1939 | Bowers | A61F 9/06 2/8.1 |
| 2,169,745 A | 8/1939 | Shipman | |
| 2,194,492 A | 3/1940 | Bowers | |
| 2,358,978 A | 9/1944 | Huntsman | |

(Continued)

FOREIGN PATENT DOCUMENTS

| AU | 2010 100 565 A4 | 7/2010 |
|---|---|---|
| CN | 87216356 U | 8/1988 |

(Continued)

OTHER PUBLICATIONS

International Search Report and Written Opinion for PCT/US2816/828219 dated Jul. 6, 2016, 11 pages.

(Continued)

*Primary Examiner* — Heather Mangine
(74) *Attorney, Agent, or Firm* — Klintworth & Rozenblat IP LLP

(57) ABSTRACT

A system for attaching a welding face member to a hard hat includes a hard hat and an adapter. The adapter is attached to the hard hat. The adapter includes an adapter mating member which attaches to a welding face member. The adapter mating member is located below the hard hat.

15 Claims, 8 Drawing Sheets

(56) References Cited

U.S. PATENT DOCUMENTS

| | | | | |
|---|---|---|---|---|
| 2,362,610 A * | 11/1944 | Bowers | A61F 9/06 | 2/8.1 |
| 2,402,431 A * | 6/1946 | Morow | A61F 9/06 | 2/8.1 |
| 2,411,831 A | 11/1946 | Lehmberg et al. | | |
| 2,421,427 A * | 6/1947 | Mamlin | A42B 3/225 | 2/5 |
| 2,447,083 A * | 8/1948 | Moeller | A42B 3/225 | 2/8.1 |
| 2,487,848 A | 11/1949 | Bowers | | |
| 2,578,171 A * | 12/1951 | Bub | A42B 3/225 | 2/8.1 |
| 2,631,286 A * | 3/1953 | Bowers | A42B 3/225 | 2/8.1 |
| 2,658,200 A | 11/1953 | Bowers, Sr. | | |
| 2,700,158 A | 1/1955 | Larsen | | |
| 2,758,307 A * | 8/1956 | Treiber | A61F 9/025 | 2/9 |
| 2,763,006 A | 9/1956 | Amundsen | | |
| 2,763,863 A * | 9/1956 | Bowers, Sr. | A42B 3/14 | 2/417 |
| 2,798,222 A * | 7/1957 | Evans | A42B 3/225 | 2/9 |
| 2,834,017 A * | 5/1958 | Simpson | A42B 3/225 | 2/10 |
| 2,915,756 A * | 12/1959 | Rex | A61F 9/06 | 2/8.1 |
| 3,060,444 A * | 10/1962 | Hoffmaster | A42B 3/225 | 2/8.1 |
| 3,074,072 A | 1/1963 | Edwards et al. | | |
| 3,075,201 A * | 1/1963 | Lindblom | A61F 9/06 | 2/8.1 |
| 3,214,768 A * | 11/1965 | Bohner | A42B 3/225 | 2/10 |
| 3,332,086 A * | 7/1967 | Simpson | A42B 3/225 | 2/8.1 |
| 3,373,444 A * | 3/1968 | Militello | A42B 3/185 | 2/10 |
| 3,380,073 A * | 4/1968 | Mclaughlin | A61F 9/06 | 2/8.1 |
| 3,430,262 A * | 3/1969 | Raschke | A42B 3/225 | 2/8.1 |
| 3,430,263 A | 3/1969 | Newcomb | | |
| 3,475,766 A * | 11/1969 | Raschke | A42B 3/225 | 2/9 |
| 3,548,412 A * | 12/1970 | Raschke | A42B 3/225 | 2/10 |
| 3,570,010 A * | 3/1971 | Hoffmaster et al. | A61F 9/025 | 2/424 |
| 3,577,564 A * | 5/1971 | Hill | A42B 3/22 | 2/10 |
| 3,594,816 A * | 7/1971 | Webb | A42B 3/225 | 2/10 |
| 3,609,765 A | 10/1971 | Molitoris | | |
| 3,696,442 A | 10/1972 | Amundsen | | |
| 3,703,750 A * | 11/1972 | Irwin, Jr. | A42B 3/185 | 24/265 R |
| 3,781,915 A * | 1/1974 | Menold | A42B 3/185 | 2/10 |
| 3,797,041 A * | 3/1974 | Raschke | A42B 3/225 | 2/8.1 |
| 3,805,294 A * | 4/1974 | Rose | A42B 3/225 | 2/10 |
| 3,868,727 A | 3/1975 | Paschall | | |
| 3,881,478 A * | 5/1975 | Rosendahl | A42B 3/0406 | 128/200.28 |
| 3,946,466 A * | 3/1976 | Sakai | A42B 3/166 | 24/568 |
| 4,040,123 A * | 8/1977 | Williams | A61F 9/06 | 2/10 |
| 4,109,320 A * | 8/1978 | Anderson | A42B 3/04 | 2/10 |
| 4,117,553 A * | 10/1978 | Bay | A42B 3/225 | 2/10 |
| 4,117,554 A | 10/1978 | Palumbo | | |
| 4,193,133 A * | 3/1980 | Laibach | A42B 3/185 | 2/10 |
| 4,293,757 A | 10/1981 | Niemi | | |
| D270,642 S | 9/1983 | Watts | | |
| 4,442,551 A * | 4/1984 | Hellberg | A42B 3/225 | 2/10 |
| 4,479,738 A * | 10/1984 | Kubnick | A42B 3/04 | 2/10 |
| 4,499,630 A | 2/1985 | Harris | | |
| 4,536,892 A * | 8/1985 | Brinkhoff | A42B 3/225 | 2/10 |
| 4,686,712 A | 8/1987 | Spiva | | |
| 4,726,074 A * | 2/1988 | Baclit | A42B 1/247 | 2/10 |
| 4,764,989 A * | 8/1988 | Bourgeois | A42B 3/185 | 2/10 |
| 4,766,609 A * | 8/1988 | Lane | A42B 3/225 | 2/424 |
| 4,793,001 A * | 12/1988 | Accardi | A61F 9/025 | 2/418 |
| 4,853,973 A | 8/1989 | Boochard | | |
| 4,928,324 A * | 5/1990 | Evans | A42B 3/225 | 2/10 |
| D316,020 S | 4/1991 | Fushiya | | |
| 5,003,632 A | 4/1991 | Claude | | |
| 5,012,528 A * | 5/1991 | Pernicka | A42B 3/225 | 2/10 |
| 5,040,528 A | 8/1991 | O'Neill | | |
| 5,044,019 A | 9/1991 | Shewchenko | | |
| 5,052,054 A * | 10/1991 | Birum | A42B 1/061 | 2/10 |
| 5,077,836 A | 1/1992 | Idoff et al. | | |
| 5,105,475 A * | 4/1992 | Lynd | A42B 3/185 | 2/10 |
| D329,590 S | 9/1992 | Chapman | | |
| 5,341,516 A * | 8/1994 | Keim | A42B 3/185 | 2/424 |
| 5,373,583 A * | 12/1994 | Birum | A42B 1/247 | 2/10 |
| 5,386,592 A | 2/1995 | Checkeroski | | |
| 5,412,811 A | 5/1995 | Hildenbrand | | |
| D365,666 S | 12/1995 | Gumpp | | |
| 5,658,065 A * | 8/1997 | Jamieson | A42B 3/04 | 2/422 |
| 5,673,431 A * | 10/1997 | Batty | A42B 3/225 | 2/10 |
| 5,724,119 A | 3/1998 | Leight | | |
| D393,933 S | 4/1998 | Huh | | |
| 5,752,280 A | 5/1998 | Hill | | |
| 5,806,101 A * | 9/1998 | Thurwanger | A61F 9/06 | 2/206 |
| 5,845,341 A * | 12/1998 | Barthold | A42B 3/04 | 2/424 |
| 5,926,854 A * | 7/1999 | Grilliot | A61F 9/025 | 2/422 |
| 5,937,439 A * | 8/1999 | Barthold | A42B 3/04 | 2/10 |
| 5,940,891 A * | 8/1999 | Lane | A61F 9/025 | 2/10 |
| 5,966,738 A * | 10/1999 | Wang Lee | A42B 3/225 | 2/10 |
| D421,116 S | 2/2000 | Mattila | | |
| 6,032,297 A | 3/2000 | Barthold | | |
| 6,035,451 A | 3/2000 | Burns | | |
| 6,041,435 A | 3/2000 | Paulson et al. | | |
| 6,055,983 A | 5/2000 | Metzger | | |
| D433,751 S | 11/2000 | Reischel | | |
| 6,154,881 A | 12/2000 | Lee | | |
| 6,260,197 B1 | 7/2001 | Hoogewind | | |
| 6,264,392 B1 | 7/2001 | Wise | | |
| D449,103 S | 10/2001 | Legare | | |
| 6,341,382 B1 | 1/2002 | Ryvin et al. | | |
| 6,352,383 B1 * | 3/2002 | Ristola | A42B 3/04 | 403/254 |

(56) References Cited

U.S. PATENT DOCUMENTS

| | | |
|---|---|---|
| 6,367,085 B1 | 4/2002 | Berg |
| 6,393,617 B1 | 5/2002 | Paris |
| D465,568 S | 11/2002 | Petherbridge |
| D467,489 S | 12/2002 | Rubinson |
| D492,559 S | 7/2004 | Itano |
| 6,782,558 B1 | 8/2004 | Keen, Sr. et al. |
| 6,807,679 B1 | 10/2004 | Wang-Lee |
| 6,892,393 B1* | 5/2005 | Provost .................. A42B 3/185 2/10 |
| 6,973,676 B1 | 12/2005 | Simpson |
| 6,996,846 B1* | 2/2006 | Karapetyan ......... A41D 13/1184 2/10 |
| D520,856 S | 5/2006 | Osiecki |
| D520,859 S | 5/2006 | Osiecki |
| D521,190 S | 5/2006 | Wu |
| 7,089,603 B2 | 8/2006 | Ketterer et al. |
| D530,185 S | 10/2006 | Osiecki |
| 7,120,939 B1 | 10/2006 | Howard |
| D543,828 S | 6/2007 | Strutin-Belinoff |
| D557,128 S | 12/2007 | Sawdon |
| 7,441,282 B2 | 10/2008 | Heine |
| D589,654 S | 3/2009 | Juhlin |
| D589,776 S | 4/2009 | Camp |
| D590,232 S | 4/2009 | Demers |
| D600,094 S | 9/2009 | Hwang |
| D617,459 S | 6/2010 | Bogue |
| D626,963 S | 11/2010 | Kim |
| D632,944 S | 2/2011 | Kang |
| 8,205,985 B1* | 6/2012 | Barajas ................... G02C 5/143 2/10 |
| 8,214,920 B1* | 7/2012 | Edgar ..................... A42B 3/225 2/422 |
| 8,245,320 B2 | 8/2012 | Provost et al. |
| D667,173 S | 9/2012 | Juhlin |
| 8,286,269 B2* | 10/2012 | Springer ................. A42B 3/185 2/10 |
| 8,321,962 B2 | 12/2012 | Moyses |
| 8,336,114 B1 | 12/2012 | Lee |
| D674,150 S | 1/2013 | Juhlin |
| D676,551 S | 2/2013 | Desai |
| 8,381,312 B2 | 2/2013 | Seo |
| D684,252 S | 6/2013 | Okada |
| D687,215 S | 8/2013 | Padgett et al. |
| 8,584,265 B2 | 11/2013 | Lilenthal |
| D696,498 S | 12/2013 | Padgett et al. |
| 8,677,517 B1* | 3/2014 | Morency ................ A42B 3/221 2/15 |
| D710,546 S | 8/2014 | Wu |
| D722,259 S | 2/2015 | Conner |
| 8,990,963 B2 | 3/2015 | Matthews |
| 9,125,448 B2 | 9/2015 | Klotz |
| 9,155,923 B2 | 10/2015 | Proctor |
| 9,427,040 B2 | 8/2016 | Leyland |
| D767,829 S | 9/2016 | Wu |
| 9,516,911 B2* | 12/2016 | Happel .................... A42B 3/04 |
| 2003/0135911 A1 | 7/2003 | Wang Lee |
| 2004/0179149 A1 | 9/2004 | Wang-Lee |
| 2004/0181856 A1* | 9/2004 | Oleson ..................... A42B 3/04 2/424 |
| 2006/0080761 A1* | 4/2006 | Huh ........................ A42B 3/04 2/424 |
| 2006/0225187 A1 | 10/2006 | Wu |
| 2007/0113318 A1 | 5/2007 | Weston |
| 2007/0220649 A1 | 9/2007 | Huh |
| 2008/0060102 A1 | 3/2008 | Matthews |
| 2008/0092342 A1* | 4/2008 | Chen ....................... A42B 3/185 24/3.12 |
| 2009/0013439 A1* | 1/2009 | Thoman ................. A42B 3/185 2/10 |
| 2009/0210989 A1 | 8/2009 | Becker et al. |
| 2009/0268153 A1* | 10/2009 | Wang-Lee ............. A42B 3/185 351/155 |
| 2010/0050325 A1 | 3/2010 | Wang-Lee |
| 2010/0154093 A1* | 6/2010 | Provost .................. A42B 3/185 2/10 |
| 2010/0229286 A1 | 9/2010 | Ahlgren |
| 2010/0235971 A1 | 9/2010 | Ahlgren |
| 2011/0101890 A1 | 5/2011 | Robinson |
| 2011/0167542 A1 | 7/2011 | Bayne |
| 2011/0225707 A1* | 9/2011 | Millios .................. A42B 3/185 2/422 |
| 2012/0084904 A1 | 4/2012 | Paulson |
| 2012/0144565 A1 | 6/2012 | Huh |
| 2012/0246807 A1* | 10/2012 | Klotz ....................... A42B 3/04 2/422 |
| 2013/0031693 A1* | 2/2013 | Gleason ................. A42B 3/225 2/9 |
| 2014/0298557 A1 | 10/2014 | Townsend, Jr. |
| 2015/0033430 A1 | 2/2015 | Hofer Kraner |
| 2015/0113712 A1 | 4/2015 | Hirschmann, Jr. et al. |
| 2015/0143618 A1* | 5/2015 | Pereira ..................... A42B 1/24 2/417 |
| 2015/0335093 A1* | 11/2015 | Curci ...................... A42B 3/225 2/424 |
| 2016/0066643 A1* | 3/2016 | Squair .................... A42B 3/225 2/424 |
| 2016/0081856 A1 | 3/2016 | Hofer-Kraner |
| 2016/0360821 A1 | 12/2016 | Benton |
| 2018/0249779 A1* | 9/2018 | DeLima ................. A42B 3/225 |

FOREIGN PATENT DOCUMENTS

| | | |
|---|---|---|
| EP | 1136007 A2 | 9/2001 |
| FR | 2187247 A1 | 1/1974 |
| JP | 6373323 U1 | 5/1988 |
| WO | 2008/025083 A1 | 3/2008 |
| WO | 2014160149 A2 | 10/2014 |

OTHER PUBLICATIONS

European Patent Office English Language Translation of FR 2187247, Mussidan Manufu Ture, Jan. 18, 1974, translated by EPO on Mar. 20, 2017.

Extended European Search Report for Application No. 16169420.3 dated Oct. 21, 2016, 8 pages.

Anonymous: "New optrel weldcap Bump Cap provides additional head protection for welders and metal fabricators", May 15, 2015, pp. 1-2, XP055308892, retrieved from the Internet: URL:http://www.ishn.com/articles/101440-new-optrel-weldcap-bump-cap-provides-additional-head-protection-for-weldeers-and-metal-fabricators.

International Search Report and Written Opinion for PCT/US2015/065213 dated Mar. 16, 2016, 13 pages.

Office action from Canadian patent Application 2,928,853 dated Feb. 1, 2017, four pages.

Communication under Rule 71(3) EPC for European Patent Application No. 15 731 219.0-1122, dated Jan. 14, 2021, 5 pages.

* cited by examiner

HARD HAT ADAPTER FOR A WELDING FACE MEMBER

CROSS-REFERENCE TO RELATED APPLICATIONS

This application is a divisional application of U.S. application Ser. No. 14/738,339, filed Jun. 12, 2015, entitled "Hard Hat Adapter for a Welding Face Member", incorporated herein by reference in its entirety.

FIELD OF THE DISCLOSURE

The disclosure relates to systems and methods for attaching a welding face member to a hard hat.

BACKGROUND

During welding, a welding face member such as welding goggles or a welding helmet, may be attached to a hard hat to protect the user's eyes while providing protection to the user's head from falling objects. Typically the strap of the welding face member is attached around a perimeter of the hard hat with the strap angling down, at a non-horizontal angle, to hold the welding face member in place against the user's face covering the user's eyes. This torque, created by the angled strap on the welding face member, may be uncomfortable to a user's face. Moreover, this torque may make it difficult to install, reposition, and remove the welding face member from the user's face. In addition, installation of the welding face member is cumbersome if the strap is positioned around the back of the user's head in addition to the placement of the hard hat headgear strap, therefore affecting comfort, fit, or proper fit of the hard hat.

A system and method is needed to reduce or eliminate one or more issues of one or more of the current systems and methods.

SUMMARY

In one embodiment, a system is disclosed for attaching a welding face member to a hard hat. The system includes a hard hat and an adapter. The adapter is attached to the hard hat. The adapter includes an adapter mating member which attaches to the welding face member. The adapter mating member is located below the hard hat.

In another embodiment, a system is disclosed for attaching a welding face member to a hard hat. The system includes a welding face member, a hard hat, and an adapter attached to the hard hat. The adapter includes an adapter mating member attached to the welding face member at a location below the hard hat In still another embodiment, a method of attaching a welding face member to a hard hat is disclosed. In one step, a welding face member is attached to an adapter mating member of an adapter attached to a hard hat. The adapter mating member is located below the hard hat.

The scope of the present disclosure is defined solely by the appended claims and is not affected by the statements within this summary.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

DETAILED DESCRIPTION

Figure 1:
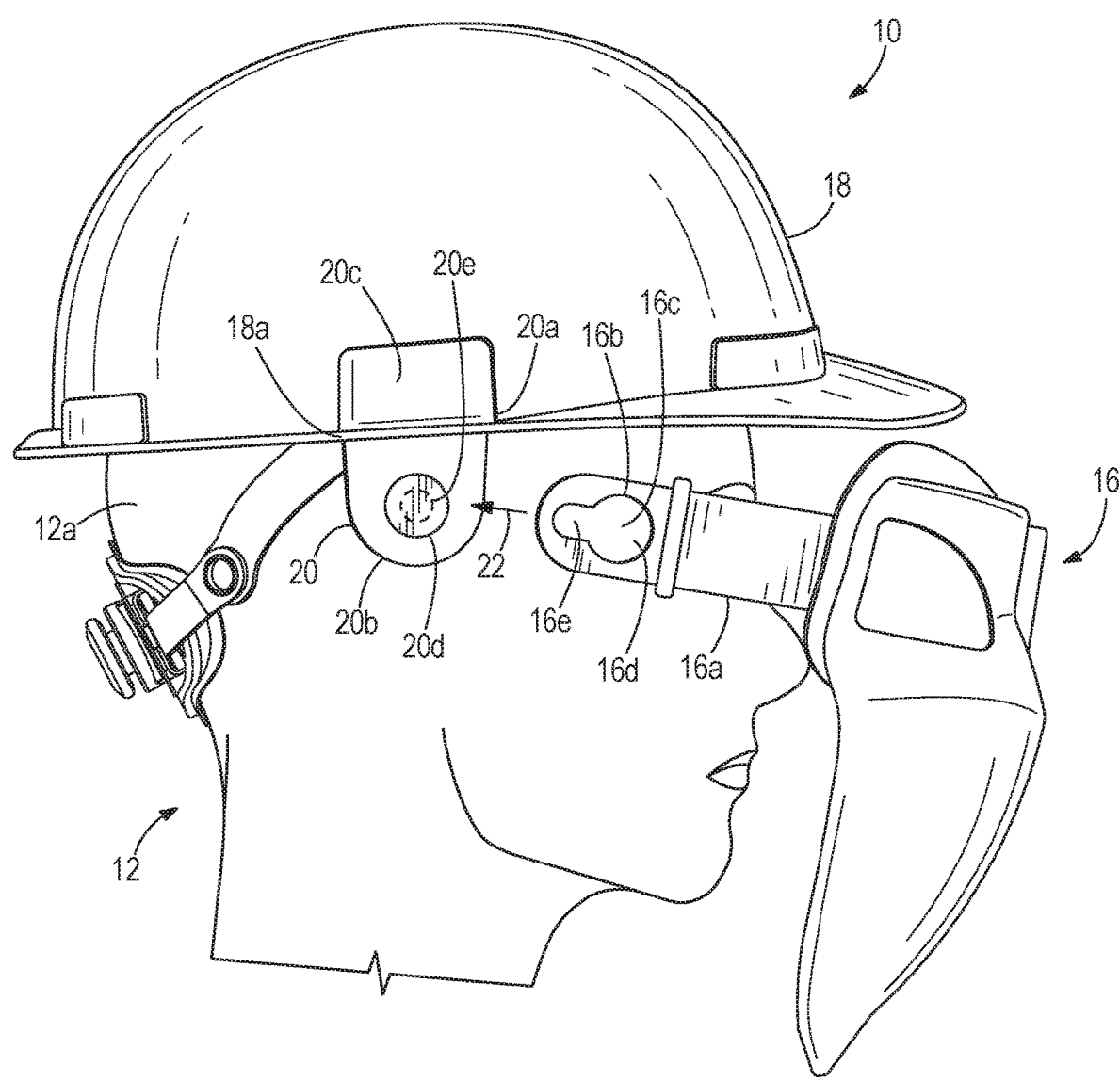
FIG. 1 is a side view illustrating one embodiment of a system, for attaching a welding face member to a hard hat, in the process of being attached to a head of a user.

FIG. 1 is a side view illustrating one embodiment of a system 10, for attaching a welding face member 16 to a hard hat 18, in the process of being attached to a head 12a of a user 12. The system 10 includes a welding face member 16, a hard hat 18, and an adapter 20. The term "welding face member" is defined as a face member which is used to protect a user's eyes during a welding process which includes welding goggles, a welding helmet, and other types of welding face members. The term "hard hat," as known in the art, is defined as a hat that is primarily used in industrial and commercial sites to protect a user's head from injury due to falling objects, impact with other objects, debris, rain, and electric shock. A first end 20a of the adapter 20 is attached to the hard hat 18, and a second end 20b of the adapter 20 is configured to be attached to a strap 16a of the welding face member 16. The first end 20a of the adapter 20 comprises a tab 20c which is inserted into and attached to a slot 18a of the hard hat 18.

The second end 20b of the adapter 20 comprises an adapter mating member 20d that is configured to be attached at a location 22 below the hard hat 18 to a strap mating member 16b of the strap 16a of the welding face member 16. The adapter mating member 20d comprises a male member 20e. The strap mating member 16b comprises a hole 16c in a shape of a key having a larger portion 16d and a smaller portion 16e. To attach the welding face member 16 to the hard hat 18, the male member 20e of the adapter mating member 20d is inserted into the larger portion 16d of the hole 16c of the strap mating member 16b and then the male member 20e is slid into the smaller portion 16e of the hole 16c of the strap mating member 16b to lock the strap mating member 16b to the adapter mating member 20d. It is noted that the mating configuration of the adapter mating member 20d and the strap mating member 16b allows the user to rotate or pivot the welding face member 16 relative to the adapter 20 and the hard hat 18 for easy attachment, repositioning to a top of the hard hat 18 during non-use, and removal of the welding face member 16 relative to the hard hat 18.

Figure 2:
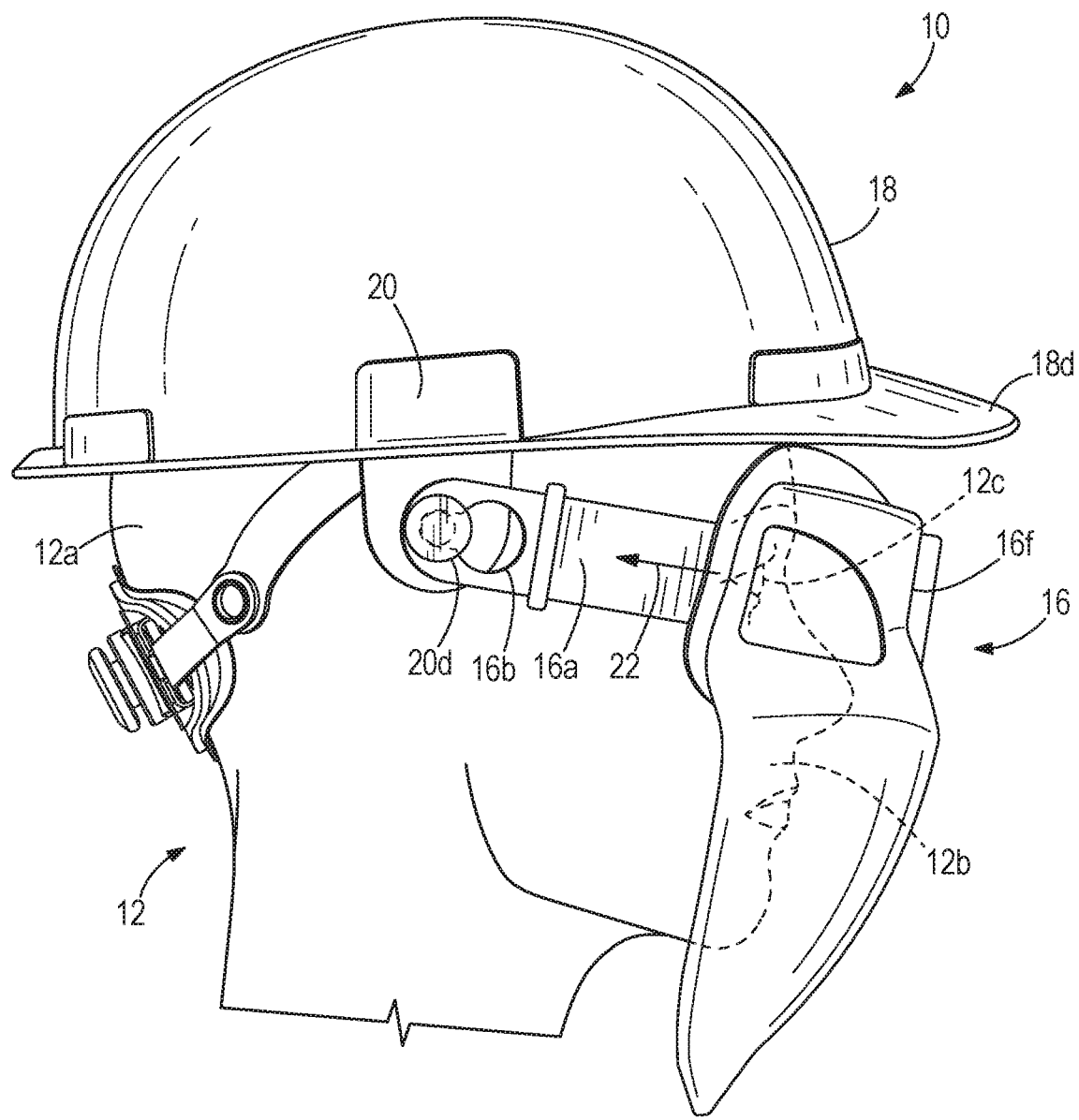
FIG. 2 is a side view illustrating the system of FIG. 1 attached to the head of the user.

FIG. 2 is a side view illustrating the system 10 of FIG. 1 attached to the head 12a of the user 12. As shown, the hard hat 18 is disposed on the head 12a of the user 12 and the adapter mating member 20d is locked to the strap mating member 16b causing the strap 16a to hold the welding face member 16 directly, with a horizontal force 22, against a face 12b of the user 12. The welding face member 16, including the shield 16f of the welding face member 16, is disposed under the brim 18d of the hard hat 18. Both the adapter mating member 20d and the strap 16a are located behind the eyes 12c of the user 12 in a same horizontal plane as the eyes 12c of the user 12. By holding the welding face member 16 with a horizontal force 22 directly against the face 12b of the user 12 due to the use of the adapter 20 extending below the hard hat 18, the welding face member 16 is more comfortable and secure than had the strap 16a of the welding face member 16 been attached directly to the hard hat 18 without the use of the adapter 20 which would have caused the welding face member 16 to be held against the user's face 12b with an angled, non-horizontal force or if the strap 16a was simply placed around the back of the head 12a, therefore causing interference with the hard hat headgear.

Figure 3:
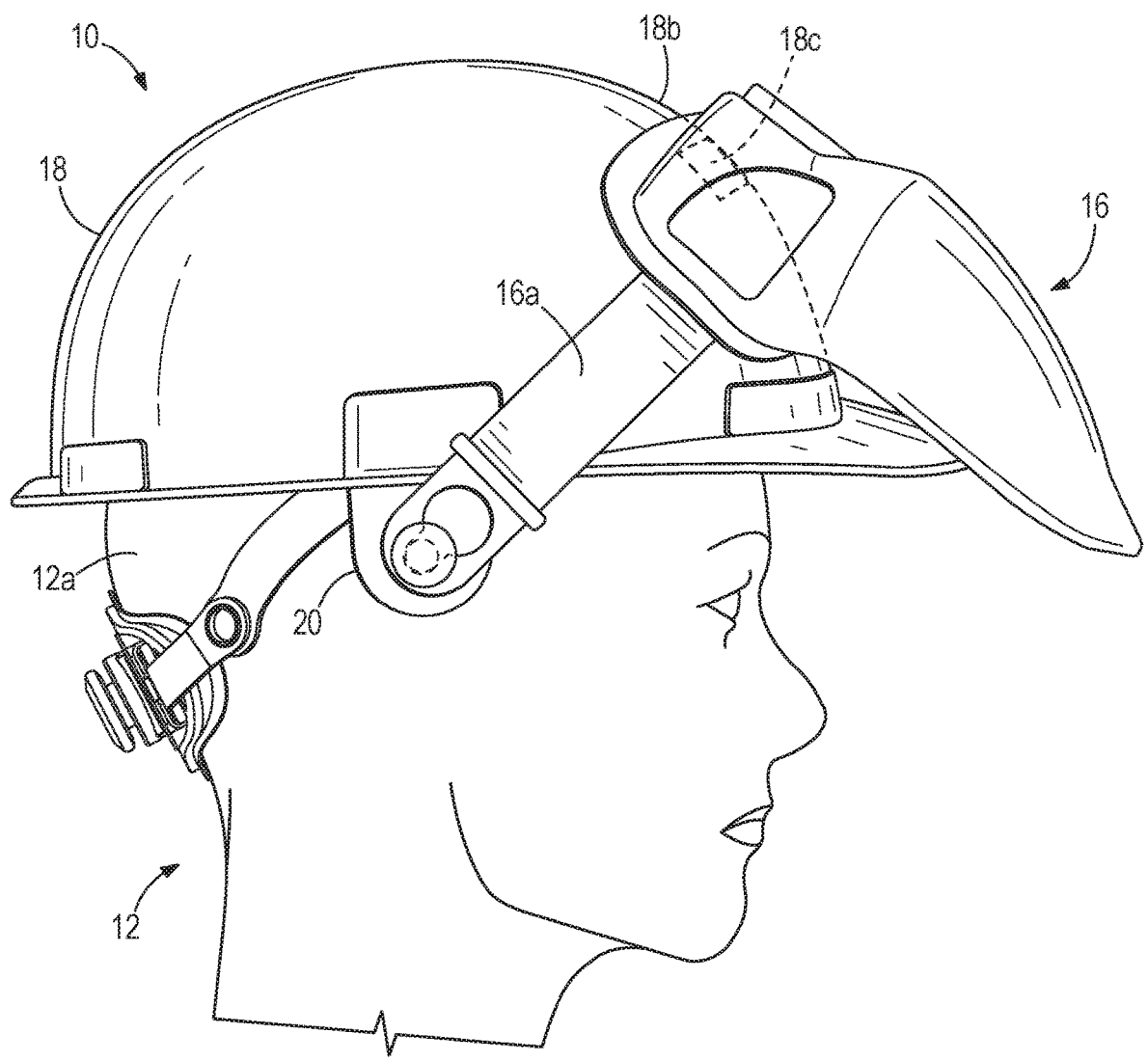
FIG. 3 is a side view illustrating the system of FIG. 1 with the welding face member disposed in an upward position and secured to a top portion of a hard hat.

FIG. 3 is a side view illustrating the system 10 of FIG. 1 with the welding face member 16 disposed in an upward position and secured to a top portion 18b of the hard hat 18. As shown, the strap 16a has been rotated/pivoted relative to the adapter 20 to dispose the welding face member 16 in the upward position when the welding face member 16 is not in use. A securement member 18c at the top portion 18b of the hard hat 18 is attached to the welding face member 16 securing the welding face member 16 to the top portion 18b of the hard hat 18. The securement member 18c may comprise any type of securement member such as a pin, a tab, a snap, a hole, a raised surface, an increased friction creating surface, or another type of securement member for attaching the welding face member 16 to the top portion 18b of the hard hat 18. In another embodiment, the securement member may be attached to the welding face member 16 itself such as a silicone eye skirt or another type of increased friction creating surface. In other embodiments, the system 10, including any of its components, of FIGS. 1-3 may vary.

Figure 4:
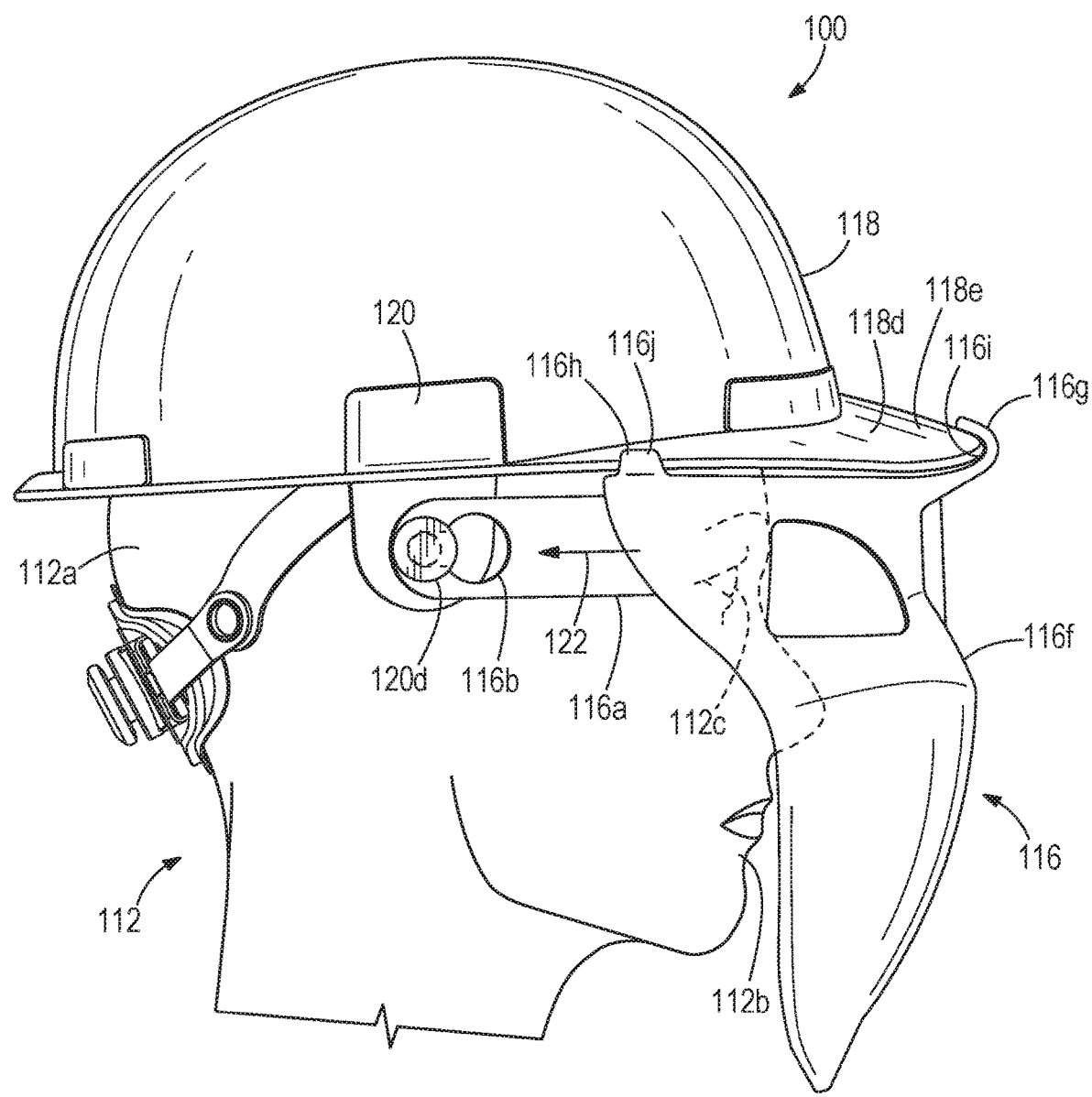
FIG. 4 is a side view illustrating another embodiment of a system, for attaching the welding face member to a hard hat, attached to a head of a user.

FIG. 4 is a side view illustrating another embodiment of a system 100, for attaching a welding face member 116 to a hard hat 118, attached to a head 112a of a user 112. The system 100 includes a welding face member 116, a hard hat 118, and an adapter 120. The hard hat 118 and the adapter 120 are identical to the hard hat 18 and the adapter 20 of the embodiment of FIGS. 1-3. The welding face member 116 differs from the welding face member 16 of the embodiment of FIGS. 1-3 in that the shield 116f of the welding face member 116 comprises attachment members 116g and 116h. Attachment member 116g comprises a trough 116i. Attachment member 116h comprises a tab 116j. A front anchor member 118e, comprising a brim 118d, of the hard hat 118 is disposed within the trough 116i of the attachment member 116g, and the tab 116j of the attachment member 116h abuts against the front anchor member 118e, comprising the brim 118d, of the hard hat 118. As a result, the shield 116f of the welding face member 116 is held apart from the face 112b of the user 112. As in the embodiment of FIGS. 1-3 the adapter mating member 120d of the adapter 120 is attached to the strap mating member 116b of the strap 116a locking the strap mating member 116b to the adapter mating member 120d.

In such manner, the shield 116f of the welding face member 116 is held firmly, with a horizontal force 122, against the front anchor member 118e of the hard hat 118 apart from the face 112b of the user 112. Both the adapter mating member 120d and the strap 116a are located behind the eyes 112c of the user 112 in a same horizontal plane as the eyes 112c of the user 112. By holding the shield 116f of the welding face member 116 with a horizontal force 122 against the front anchor member 118e of the hard hat 118 due to the use of the adapter 120 extending below the hard hat 118, the welding face member 116 does not put any pressure on the face 112b of the user 112 and is more secure and in a more optimal vertical position than had the strap 116a of the welding face member 116 been attached directly to the hard hat 118 without the use of the adapter 120 which would have caused the welding face member 116 to be held against the front anchor member 118e of the hard hat 118 at an angle. In other embodiments, the system 100, including any of its components, of FIG. 4 may vary.

Figure 5:
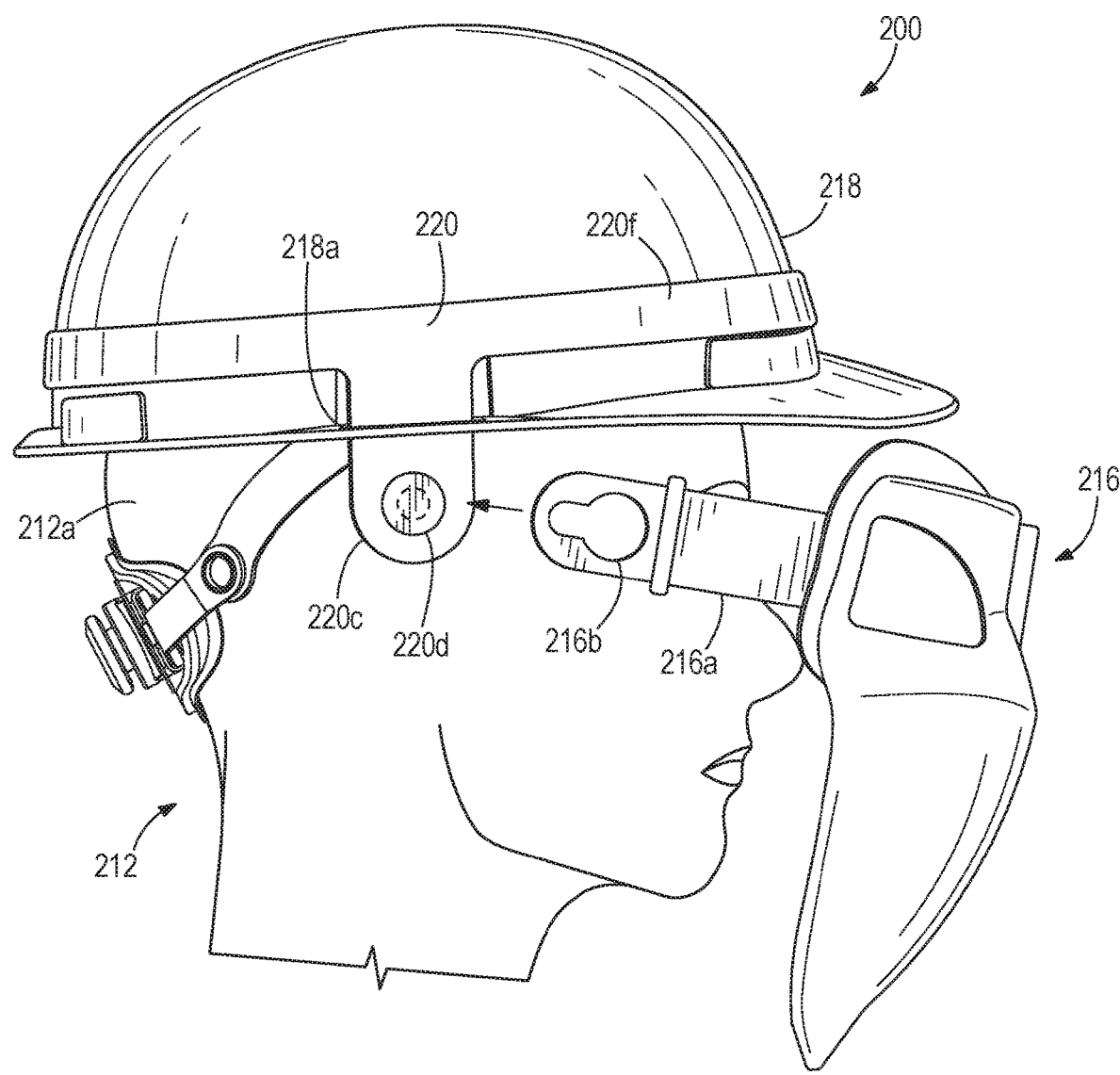
FIG. 5 is a side view illustrating another embodiment of a system, for attaching the welding face member to a hard hat, in the process of being attached to a head of a user.

FIG. 5 is a side view illustrating another embodiment of a system 200, for attaching a welding face member 216 to a hard hat 218, in the process of being attached to a head 212a of a user 212. The system 200 includes a welding face member 216, a hard hat 218, and an adapter 220. The hard hat 218 and the welding face member 216 are identical to the hard hat 18 and the welding face member 16 of the embodiment of FIGS. 1-3 with the exception that the hard hat 218 does not have slots (depicted as slot 18a in FIGS. 1-3). The adapter 220 differs from the adapter 20 of the embodiment of FIGS. 1-3 in that the tab 220c of the adapter 220 is attached to a ring member 220f which abuts against and extends around a perimeter of the hard hat 218. The ring member 220f allows the adapter 220 to be quickly attached to the hard hat 218 by sliding the ring member 220f over the hard hat 218 so that it abuts and extends around the perimeter of the hard hat 218, and then by extending the tab 220c of the adapter 220 down past the bottom perimeter of the hard hat 218. Subsequently, the adapter 220 may be attached to the welding face member 216 by attaching the adapter mating member 220d of the adapter 220 to the strap mating member 216b of the strap 216a of the welding face member 216.

Figure 6:
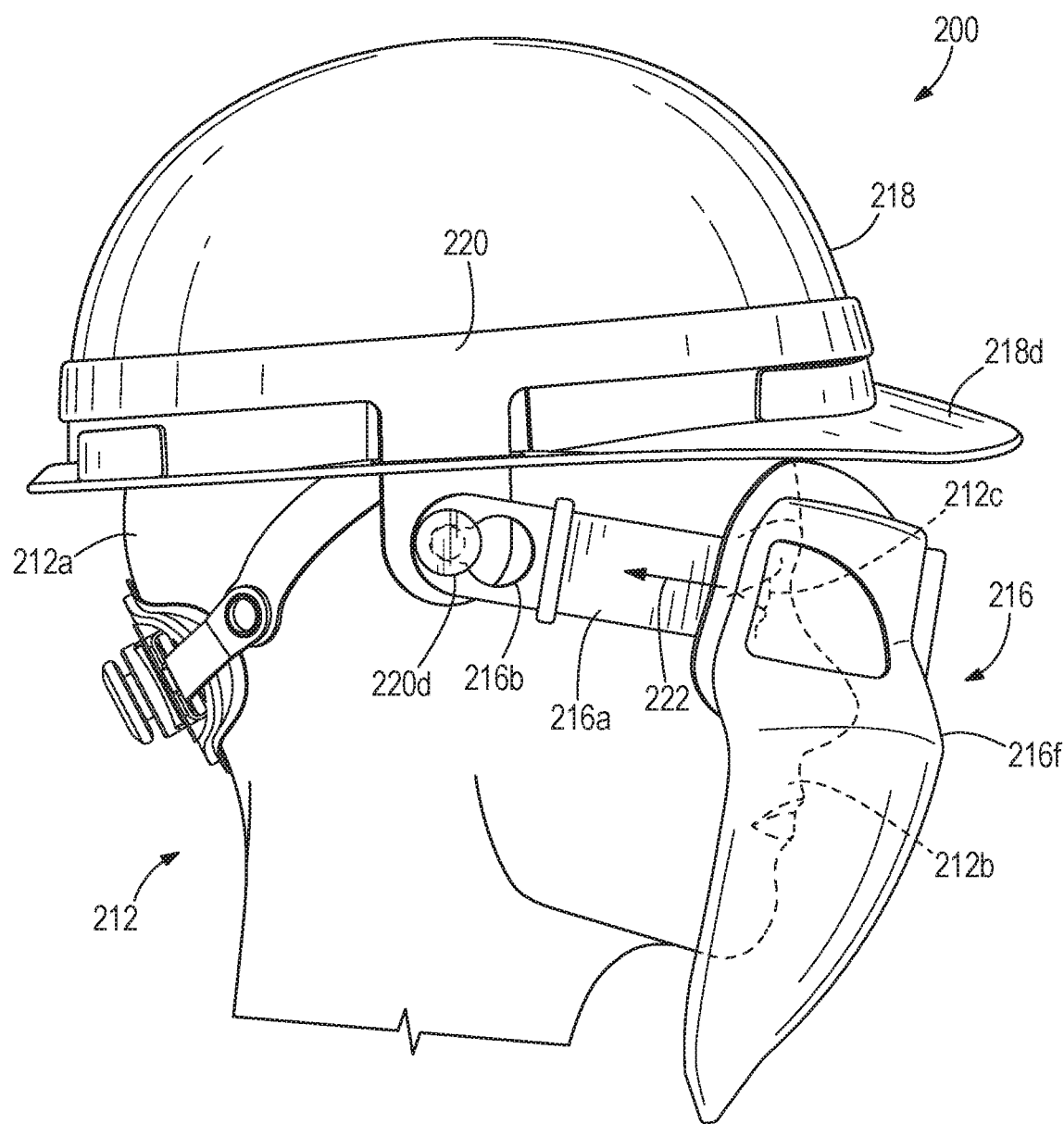
FIG. 6 is a side view illustrating the system of FIG. 5 attached to the head of the user.

FIG. 6 is a side view illustrating the system 200 of FIG. 5 attached to the head 212a of the user 212. As shown, the hard hat 218 is disposed on the head 212a of the user 212 and the adapter mating member 220d is locked to the strap mating member 216b causing the strap 216a to hold the welding face member 216 directly, with a horizontal force 222, against a face 212b of the user 212. The welding face member 216, including the shield 216f of the welding face member 216, is disposed under the brim 218d of the hard hat 218. Both the adapter mating member 220d and the strap 216a are located behind the eyes 212c of the user 212 in a same horizontal plane as the eyes 212c of the user 212. By holding the welding face member 216 with a horizontal force 222 directly against the face 212b of the user 212 due to the use of the adapter 220 extending below the hard hat 218, the welding face member 216 is more comfortable and secure than had the strap 216a of the welding face member 216 been attached directly to the hard hat 218 without the use of the adapter 220 which would have caused the welding face member 216 to be held against the user's face 212b with an angled, non-horizontal force. In other embodiments, the system 200, including any of its components, of FIGS. 5-6 may vary.

Figure 7:
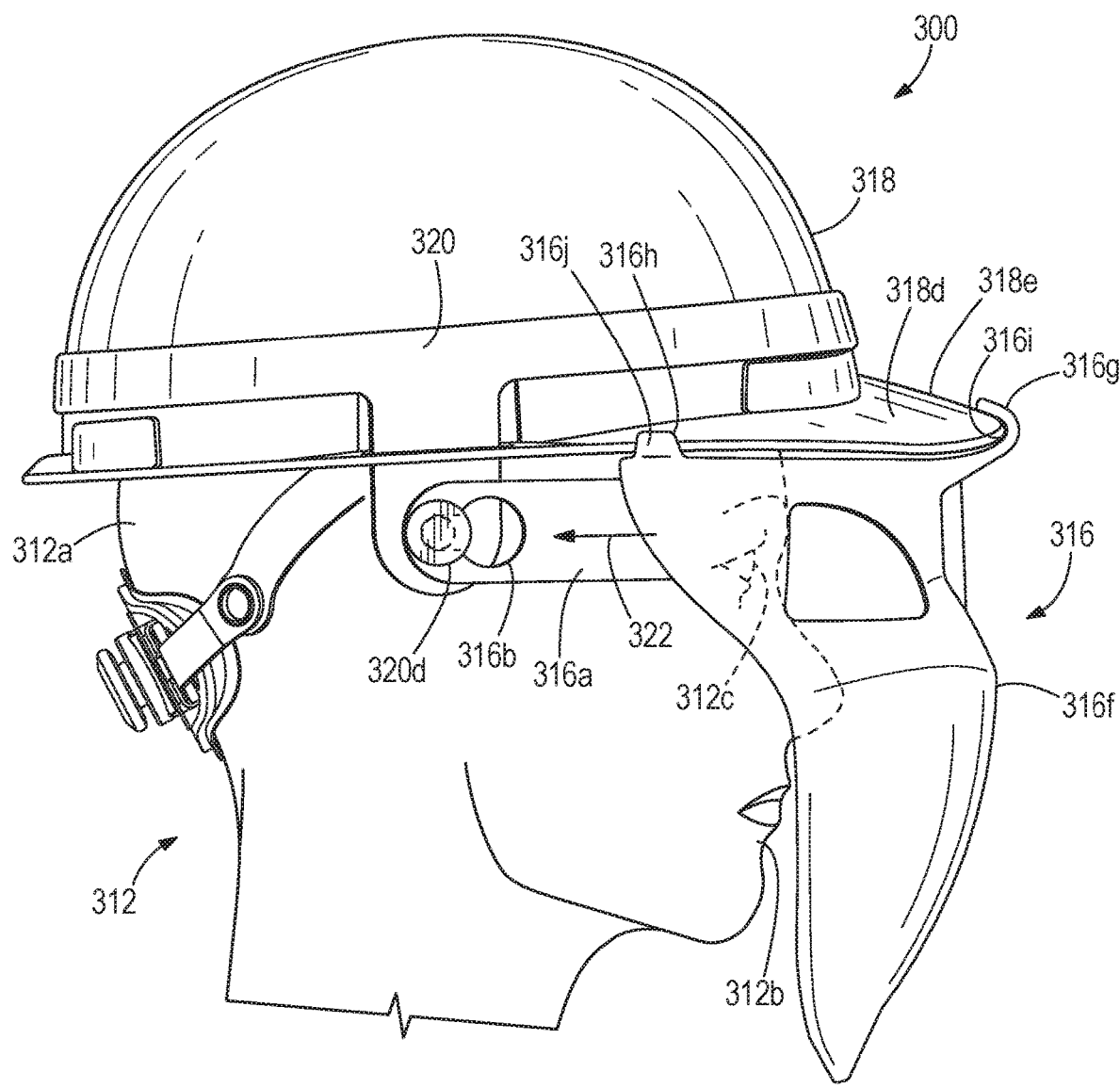
FIG. 7 is a side view illustrating another embodiment of a system, for attaching the welding face member to a hard hat, attached to a head of a user.

FIG. 7 is a side view illustrating another embodiment of a system 300, for attaching a welding face member 316 to a hard hat 318, attached to a head 312a of a user 312. The system 300 includes a welding face member 316, a hard hat 318, and an adapter 320. The hard hat 318 and the adapter 320 are identical to the hard hat 218 and the adapter 220 of the embodiment of FIG. 5-6. The welding face member 316 differs from the welding face member 216 of the embodiment of FIGS. 5-6 in that the shield 316f of the welding face member 316 comprises attachment members 316g and 316h. Attachment member 316g comprises a trough 316i. Attachment member 316h comprises a tab 316j. A front anchor member 318e, comprising a brim 318d, of the hard hat 318 is disposed within the trough 316i of the attachment member 316g, and the tab 316j of the attachment member 316h abuts against the front anchor member 318e of the hard hat 318. As a result, the shield 316f of the welding face member 316 is held apart from the face 312b of the user 312. As in the embodiment of FIGS. 5-6 the adapter mating member 320d of the adapter 320 is attached to the strap mating member 316b of the strap 316a locking the strap mating member 316b to the adapter mating member 320d.

In such manner, the shield 316f of the welding face member 316 is held firmly, with a horizontal force 322, against the front anchor member 318e of the hard hat 318 apart from the face 312b of the user 312. Both the adapter mating member 320d and the strap 316a are located behind the eyes 312c of the user 312 in a same horizontal plane as the eyes 312c of the user 312. By holding the shield 316f of the welding face member 316 with a horizontal force 322 against the front anchor member 318e of the hard hat 318 due to the use of the adapter 320 extending below the hard hat 318, the welding face member 316 does not put any pressure on the face 312b of the user 312 and are more secure and in a more optimal vertical position than had the strap 316a of the welding face member 316 been attached directly to the hard hat 318 without the use of the adapter 320 which would have caused the welding face member 316 to be held against the front anchor member 318e of the hard hat 318 at an angle. In other embodiments, the system 300, including any of its components, of FIG. 7 may vary.

Figure 8:
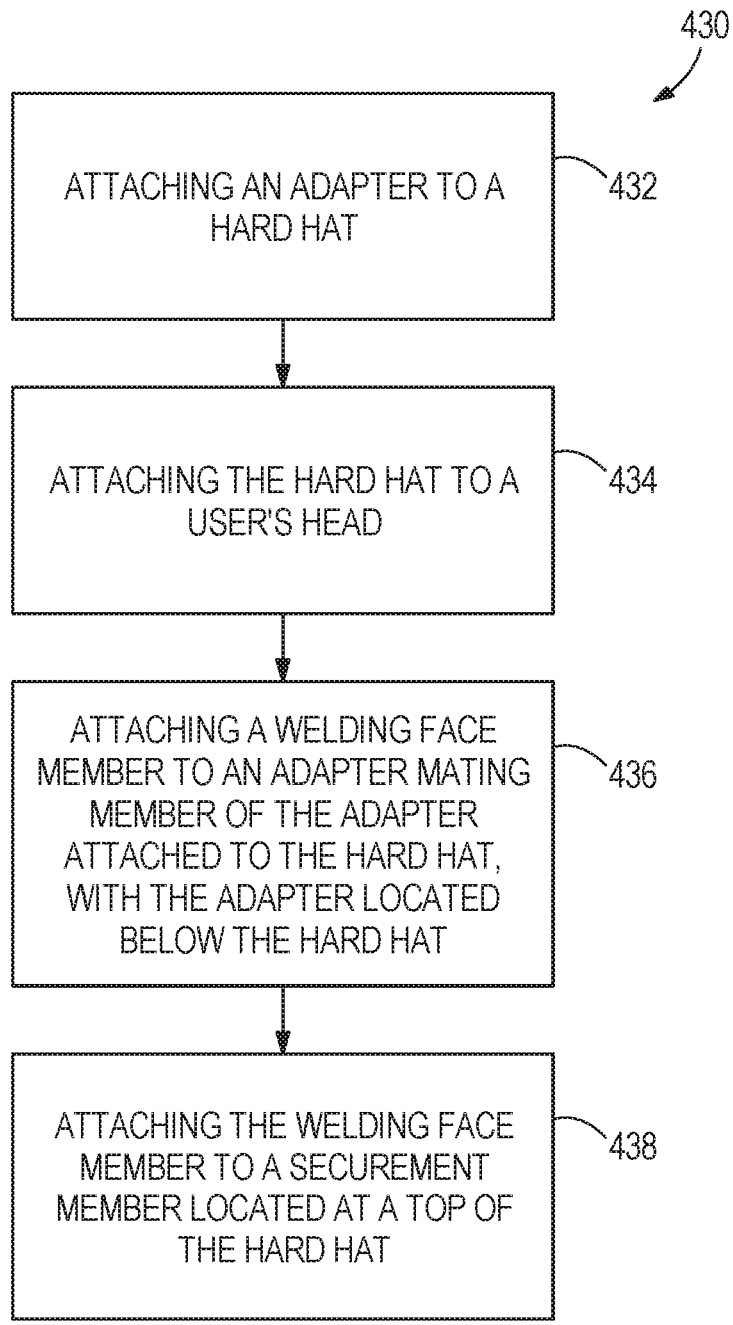
FIG. 8 illustrates a flowchart of one embodiment of a method of attaching a welding face member to a hard hat.

FIG. 8 illustrates a flowchart of one embodiment of a method 430 of attaching a welding face member to a hard hat. The method 430 may utilize any of the system disclosed herein. In other embodiments, the method may utilize varying systems. In step 432, an adapter is attached to a hard hat. In step 434, the hard hat is attached to a user's head. In step 436, a welding face member is attached to an adapter mating member of the adapter attached to the hard hat, wherein the adapter mating member is located below the hard hat. In one embodiment, step 436 further comprises holding the welding face member directly against the user's face due to the adapter. In another embodiment, step 436 further comprises holding the welding face member apart from the user's face due to a front anchor member of the hard hat being attached to an attachment member of the welding face member. In still another embodiment, step 436 further comprises the adapter mating member and a strap of the welding face member, attached to the adapter mating member located behind the user's eyes, both disposed in a same horizontal plane as the user's eyes. In yet another embodiment, step 436 further comprises attaching the adapter mating member to the welding face member using a key connection. In step 438, the welding face member is attached to a securement member located at a top of the hard hat. In other embodiments, one or more steps of the method 430 may be altered in substance or order, one or more steps of the method 430 may not be followed, or one or more additional steps may be added to the method 430.

One or more embodiments of the disclosure substantially increases the convenience of wearing a welding face member with a hard hat. One or more embodiments of the disclosure significantly improves the positioning and protection of welding eye and face protection for welders who are required to wear hard hats. One or more embodiments of the disclosure eliminates the torque placed on the hard hat fit by current strap configurations, resulting in proper hard hat wear and improved comfort. This would also allow for some gap to be disposed between the welding face member and the user's face so that safety glasses may be comfortably worn.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the disclosure is defined by the appended claims. Accordingly, the disclosure is not to be restricted except in light of the appended claims and their equivalents.

The invention claimed is:

1. A system comprising:
   a hard hat;
   a welding face member attached to hard hat;
   a first strap and a second strap attached to the welding face member, wherein the first and second straps each form a female member; and
   an adapter disposed around, against, and attached to an outer surface of the hard hat and to the strap, wherein the adapter comprises a ring member and a pair of tabs, wherein the ring member abuts against and extends around a perimeter of the outer surface of the hard hat and above a brim of the hat, wherein each tab is attached to the ring member at a predetermined and fixed position, wherein each tab extends downwards from the ring member to below the brim of the hat and through a slot in the brim of the hat, and wherein a male member of each tab is disposed below the brim of the hard hat and is attached to the female member of the strap.

2. The system of claim 1 wherein the female member of the strap comprises a key hole having a larger portion and a smaller portion which are laterally connected, and the male member of each tab of the pair of tabs of the adapter comprises a pin attached to the key hole.

3. The system of claim 2 wherein the pin is secured to, within, and against the smaller portion of the key hole securing the strap to the adapter.

4. The system of claim 3 wherein the pin is moveable from the smaller portion of the key hole to the larger portion of the key hole, the pin being smaller than the larger portion of the key hole to allow the strap to be detached from the adapter.

5. The system of claim 1 wherein a tab of the welding face member is attached to the hard hat.

6. The system of claim 5 wherein the tab of the welding face member is attached to the brim of the hard hat.

7. The system of claim 1 wherein a portion of the hard hat is disposed within and against a trough of the welding face member.

8. The system of claim 7 wherein the portion comprises the brim of the hard hat, and the brim of the hard hat is disposed within and against the trough of the welding face member.

9. The system of claim 1 wherein the strap is rotatable relative to the adapter to rotate the welding face member over the hard hat.

10. A system comprising:
a hard hat comprising a brim of the hard hat;
a welding face member comprising a first tab and a trough, the first tab attached to the brim of the hard hat, the brim of the hard hat disposed within and against the trough;
a strap attached to the welding face member; and
an adapter comprising a ring member disposed around, against and attached to an outer surface of the hard hat, the adapter comprising a second tab attached to the ring member at a predetermined and fixed position and disposed below the hard hat and through a slot in the brim of the hat, the second tab attached to the strap.

11. The system of claim 10 wherein the second tab comprises a male member, the male member of the second tab attached to a female member of the strap.

12. The system of claim 11 wherein the male member of the second tab comprises a pin and the female member of the strap comprises a key hole, the pin of the second tab attached to the key hole of the strap, the key hole having a larger portion and a smaller portion which are laterally connected.

13. The system of claim 12 wherein the pin is secured to, within, and against the smaller portion of the key hole securing the strap to the adapter.

14. The system of claim 13 wherein the pin is moveable from the smaller portion of the key hole to the larger portion of the key hole, the pin being smaller than the larger portion of the key hole to allow the strap to be detached from the adapter.

15. The system of claim 14 wherein the strap is rotatable relative to the adapter to rotate the welding face member over the brim and over a top of the hard hat.

* * * * *